United States Patent

Rose et al.

[11] Patent Number: 6,017,519
[45] Date of Patent: Jan. 25, 2000

[54] COMPOSITION FOR PERMANENT WAVING OF HUMAN HAIR

[75] Inventors: Burkhard Rose, Darmstadt; Jürgen Tennigkeit, Seeheim, both of Germany

[73] Assignee: Goldwell AG, Germany

[21] Appl. No.: 08/195,374

[22] Filed: Feb. 14, 1994

[30] Foreign Application Priority Data

Feb. 17, 1993 [DE] Germany .............................. 43 04 828
Mar. 5, 1993 [DE] Germany .............................. 43 06 915

[51] Int. Cl.⁷ ...................................................... A61K 7/09
[52] U.S. Cl. ..................................... 424/70.51; 424/70.19; 424/70.21; 424/70.31; 424/70.5; 132/210
[58] Field of Search .................................. 424/71, 72, 70, 424/70.51, 70.19, 70.21, 70.31, 70.5

[56] References Cited

U.S. PATENT DOCUMENTS

| | | | |
|---|---|---|---|
| 3,823,232 | 7/1974 | Galerne | 424/72 |
| 4,459,284 | 7/1984 | Azuma | 424/71 |
| 4,855,130 | 8/1989 | Konrad | 424/71 |
| 5,116,608 | 5/1992 | Yoshioka | 424/71 |
| 5,223,252 | 6/1993 | Kolc | 424/71 |
| 5,332,570 | 7/1994 | Bergstrom | 424/72 |

FOREIGN PATENT DOCUMENTS 2108163  5/1983  United Kingdom .

*Primary Examiner*—Thurman K. Page
*Attorney, Agent, or Firm*—Londa and Traub LLP

[57] ABSTRACT

This invention refers to a composition for permanent waving of human hair, containing thioglycolic acid or the salts thereof, preferably the ammonium salt, and comprising two compositions which are kept separate until application, whereof a Composition (A) contains at least an amino acid hydrochloride and at least one polyol or the methyl and ethyl ethers thereof, preferably 1,2-propanediol in aqueous solution, having a pH-value of preferably between about 4.5 and 6.5, and a Composition (B) which is kept separate from said Composition (A) until use contains ammonium carbonate, ammonium hydrogen carbonate, and (or) ammonium carbamate as alkalizing agent(s), having a pH-value between about 8 and 9.5, and both compositions are mixed before application whereby a pH-value between about 7 and 8 is obtained. The compositions, which are kept separate, present outstanding stability; upon application after admixture optimal waving performance and, at the same time, gentle treatment of the hair is achieved.

20 Claims, No Drawings

COMPOSITION FOR PERMANENT WAVING OF HUMAN HAIR

This invention refers to a composition for permanent waving of human hair, i.e., a permanent waving composition, showing outstanding waving performance, however, without having any damaging effect on the hair even after several applications.

As it is well-known, permanent waving requires two working steps: The reductive splitting of cystine disulfide bonds of the hair by the action of a reducing agent, and following neutralization or fixing by the application of an oxidizing agent to restore the cystine disulfide bonds.

The reducing agent predominantly used today still is thioglycolic acid, particularly its ammonium salt, although numerous other thio compounds were suggested for this purpose which, however, did not succeed in practical work.

The compositions comprising thioglycollate are normally used at a pH-value from 8 to 10, particularly 8.5 to 9.5, which may lead to hair damage when applied repeatedly in close succession.

It has already been tried to overcome these disadvantages by the development of so-called "acidic permanent waving compositions" having a pH-value at application from about 6.8 to 7.8, which is close to neutral. The reducing agent used predominantly in these compositions is thioglycolic acid monoglycerol ester. However, this substance turned out to be skin irritant and, in particular, sensitizing to some users, thus the effect of this solution was not optimal.

It has now been found that these problems may be overcome, and permanent waving compositions acting at a pH-value where no hair damage develops but still a good perming action is achieved, if a preparation is used which contains thioglycolic acid or a salt thereof, preferably ammonium thioglycollate, and comprises two separate compositions which are mixed prior to application, of which a Composition (A) contains at least one amino acid hydrochloride and at least one polyol or the methyl or ethyl ethers thereof in an aqueous base, and having a pH-value of 4.5 to 6.5, preferably between 5 and 6, most preferred 5.4 to 5.6, and a Composition (B) having a pH-value between 8 and 9.5, preferably 8.5 to 9.2, contains, as an alkalizing agent, ammonium carbonate, ammonium hydrogen carbonate and (or) ammonium carbamate, and the ready-for-use composition obtained after mixing has a pH-value from 7 to 8, preferably 7.4 to 7.6.

These compositions are stable and have only a low build-up of pressure.

As already mentioned, the composition comprises thioglycolic acid and (or) the ammonium salt thereof, however, other salts may also be incorporated, e.g., sodium thioglycollate or amine thioglycollates. The additional use of other active waving substances as they are known per se is possible but not compulsory.

Preferably, thioglycolic acid and the salts thereof are used in Composition (A).

The proportion of thioglycolic acid in the compositions of the invention is between about 4 and about 12% by weight, preferably from 6 to 9% by weight, calculated to thioglycolic acid, and related to the total composition of the ready-to-use material (Compositions A+B).

An essential ingredient of the Composition (A) is an amino acid hydrochloride which contributes within the mixture of thioglycolic acid, or the salts thereof, and polyol (s) to the adjustment of the pH-value and stabilization of the system.

A preferred amino acid hydrochloride is cysteine hydrochloride providing additionally a certain curling performance. Another preferred amino acid hydrochloride is glycine hydrochloride.

However, further amino acid hydrochlorides may also be included, e.g., those of alanine, valine, leucine, isoleucine, proline, tryptophane, phenyl alanine, methionine, serine, tyrosine, threonine, asparagine, glutamine or histidine.

The proportion of amino acid hydrochloride depends on the adjustment of the pH-value required. The minimum proportion is about 0.5% by weight, the maximum proportion about 5% by weight, calculated to pure amino acid and the total composition of the composition (which is the sum of Compositions (A) plus (B)).

The third essential ingredient in the compositions containing thioglycolic acid or the salts thereof is a polyol or an ether thereof. As such are particularly used: 1,2- or 1,3-propanediol, 1,2-, 1,3- or 1,4-butanediol and the methyl and ethyl ethers thereof, preferably 1-methoxypropanol(-2), di-propyleneglycol monomethyl ether, and glycerol.

The preferred proportion is from about 1 to 15% by weight of the total composition (Compositions A plus B), most preferred from about 2 to 10% by weight.

Composition (B) which is kept separate from the Composition (A) until application onto the hair contains ammonium carbonate, ammonium hydrogen carbonate and (or) ammonium carbamate as alkalizing agent, preferably in a quantity between about 0.5 and about 7.5% by weight, more preferred 1 to about 5, most preferred about 2 to 4% by weight, calculated to the total Composition (A) plus (B).

The permanent waving compositions according to the invention may comprise all additives proposed and used for this purpose.

To avoid repetition, reference is made to the relevant state of the art and the publications thereto, e.g., "Ullmann's Encyclopedia of Industrial Chemistry", Vol.A12 (1986), pp. 588 to 591, and the monography of K. Schrader, "Grundlagen und Rezepturen der Kosmetika", 2nd Ed. (1989, H üthig Buchverlag), pp. 823 to 840.

The neutralization of the hair curled by use of the permanent waving compositions according to the invention is performed by the known and usual neutralization methods using hydrogen peroxide or alkali bromates.

A separate housing of the two compositions according to the invention is preferably performed in two-chamber packs, as they are known since a long time, whereof the separating wall is pierced by suitable means before application.

Such two-chamber packs which are particularly suitable for the compositions according to the invention are disclosed, e.g., in German Patent Applications Nos. 35 28 525, 36 06 003, 38 12 343 and 38 37 595.

The following examples illustrate the invention.

Example 1

Composition A:

| | |
|---|---|
| Ammonium thioglycollate, 71% | 11.0 (gram) |
| Cysteine hydrochloride.$H_2O$ | 2.5 |
| 1,2-Propanediol | 2.5 |
| Ammonia, 25% | @ pH 5.5 |
| Water | @ 27.8 |

Composition B:

| | |
|---|---|
| Ammonium hydrogen carbonate | 5.0 (gram) |
| Quaternary polymer | 0.5 |
| Amphoteric surfactant (Coco-Betaine) | 0.8 |
| Diacetin | 0.2 |
| 1,3-Butanediol | 1.0 |
| 1,2-Propanediol | 0.5 |

Example 1 (continued)

| | |
|---|---|
| Nonionic surfactant | 0.8 |
| Dyestuff, opacifier, perfume | q.s. |
| Ammonia, 25% | @ pH 8.3 |
| Water | @ 72.2 |

The compositions were separately filled into dosage packs of 65 grams (composition B) and 25 grams (composition A), resp., of a known two-chamber container.

Example 2

Composition A:

| | |
|---|---|
| Ammonium thioglycollate | 18.0 (gram) |
| Glycine hydrochloride | 0.7 |
| 1,2-Propanediol or glycerol | 2.5 |
| Ammonia, 25% | @ pH 5.5 |
| Water | @ 27.8 |

Composition B:

| | |
|---|---|
| Ammonium hydrogen carbonate | 02.0 (gram) |
| Quaternary fatty alkyl ammonium chloride | 1.5 |
| Amphoteric surfactant | 0.7 |
| Ethanol | 5.0 |
| Nonionic surfactant | 0.8 |
| Diacetin | 0.6 |
| Perfume, defoaming agent, opacifier | q.s. |
| Ammonia, 25% | @ pH 8.4 |
| Water | @ 72.2 |

The compositions (A) and (B) are packed separately in a two-chamber container, as described in example 1.

Example 3

Composition A:

| | |
|---|---|
| Ammonium thioglycollate, 71% | 10.5 (gram) |
| Cysteine hydrochloride.$H_2O$ | 2.5 |
| 1,2-Propanediol | 2.5 |
| Ethanol | 2.0 |
| Ammonia, 25% | @ pH 5.6 |
| Water | @ 27.8 |

Composition B:

| | |
|---|---|
| Ammonium hydrogen carbonate | 5.0 (gram) |
| Urea | 1.0 |
| Quaternary polymer | 1.0 |
| Amphoteric surfactant | 0.8 |
| Ethanol | 5.0 |
| Diacetin | 0.3 |
| Nonionic emulsifier | 0.8 |
| Dyestuff, opacifier, perfume | q.s. |
| Ammonia, 25% | @ pH 8.4 |
| Water | @ 72.2 |

25 grams of composition (A) and 65 grams of composition (B) were packed in a two-chamber container, according to example 1.

Example 4

Composition A:

| | |
|---|---|
| Ammonium thioglycollate, 71% | 18.2 (gram) |
| Cysteine hydrochloride.$H_2O$ | 3.0 |
| 1,2-Propanediol | 2.5 |
| Ammonium 25% | @ pH 5.5 |
| Water | @ 27.8 |

Composition B:

| | |
|---|---|
| Ammonium carbonate | 2.9 (gram) |
| Quaternary polymer | 0.5 |
| Amphoteric surfactants (coco betaine) | 0.6 |
| Diacetine | 0.2 |
| Ethanol | 5.0 |
| 1,3-Butanediol | 1.0 |
| 1,2-Propanediol | 0.5 |
| Nonionic surfactant | 0.8 |
| Dyestuff, opacifier, perfume | q.s. |
| Water | @ 72.2 |

(pH: ≈ 8.75)

The compositions were filled in portions of 65 grams (Composition B) and 25 grams (Composition A) into known two-chamber packs.

Example 5

Composition A:

| | |
|---|---|
| Ammonium thioglycollate | 18.3 (gram) |
| Cysteine hydrochloride | 3.0 |
| 1,2-Propanediol or glycerol | 2.5 |
| Ammonia, 25% | @ pH 5.5 |
| Water | @ 27.8 |

Composition B:

| | |
|---|---|
| Ammonium carbamate | 0.9 (gram) |
| Quaternary polymer | 0.4 |
| Amphoteric surfactants (coco betaine) | 0.6 |
| Ethanol | 5.0 |
| Nonionic surfactant | 0.8 |
| Diacetine | 0.3 |
| Perfume, defoamer, opacifier | q.s. |
| Water | @ 72.2 |

(pH-value: 9.18)

The Compositions (A) and (B) are separately packed into a two-chamber pack, as described in Example 4.

Upon mixing one of the Compositions 1A to 5A with one of the corresponding Compositions 1B or 5B, being kept separate until application, ready-to-use mixtures of weakly alkaline pH-value in the range between about 7.4 to about 7.6 are obtained. After application of the mixture A/B onto the hair and subsequent neutralization with diluted hydrogen peroxide an outstanding permanent wave having no damaging effect on the hair even after several applications within close succession is achieved.

Example 6

Composition A:

| | |
|---|---|
| 1,2-Propanediol | 2.5 (g) |
| Cysteine hydrochloride | 2.5 |
| Ammonia, 25% | @ pH 5.5 |
| Water | @ 27.8 |

Composition B:

| | |
|---|---|
| Ammonium hydrogen carbonate | 5.0 (g) |
| Quaternary polymer | 0.5 |
| Amphoteric surfactant (Coco betaine) | 0.8 |
| Nonionic surfactant | 0.8 |
| Diacetin | 0.2 |
| 1 3-Butanediol | 1.0 |
| 1,2-Propanediol | 0.5 |
| Ammonium thioglycollate, 71% | 11.0 |

-continued

Example 6

| | |
|---|---|
| Ammonium 2-thiolactate, 50% | 2.0 |
| Dyestuff, perfume, pearling agent | q.s. |
| Ammonia, 25% | @ pH 8.0 |
| Water | @ 72.2 |

25 g of Composition (A) and 65 g of Composition (B) were, as described in the foregoing examples, packed into a two-compartment container. Upon mixing of these Compositios (A) and (B), a ready-to-use permanent wave solution with a pH-value of 7.7 was obtained.

After application onto and action on the hair and subsequent neutralization or fixation, resp., with diluted $H_2O_2$ solution, an excellent permanent wave was reached with no damaging of the hair even after repeated applications.

We claim:

1. A kit for preparing a ready-to-use composition for permanent waving of human hair, said kit comprising two separate packages,
    a first package containing a first composition comprising thioglycolic acid or a salt thereof, at least one amino acid hydrochloride, and at least one compound chosen from the group consisting of polyol, and a methyl or ethyl ether thereof in an aqueous solution, said first composition having a pH-value of about 4.5 to 6.5, and
    a second package containing a second composition comprising at least one compound chosen from the group consisting of ammonium carbonate, ammonium hydrogen carbonate and ammonium carbamate, said second composition having a pH-value of about between 8 and 9.5,
    whereby when said first and second compositions are mixed before application onto human hair, a ready-to-use composition produced thereby has a pH-value between 7 and 8.

2. The kit according to claim 1, wherein the second composition comprises 1 to 5% by weight ammonium hydrogen carbonate, as a percentage of the total weight of the first and second compositions.

3. The kit according to claim 1, wherein the first composition has a pH-value between 5.0 and 6.0.

4. The kit according to claim 1, wherein the second composition has a pH-value between 8.5 and 9.2.

5. The kit according to claim 1, wherein the ready-to-use composition has a pH-value between 7.3 and 7.7.

6. The kit according to claim 1, wherein the amino acid hydrochloride is cysteine hydrochloride.

7. The kit according to claim 1, wherein the amino acid hydrochloride is glycine hydrochloride.

8. The kit according to claim 1, wherein the first composition comprises 1 to 15% by weight of the at least one compound chosen from the group consisting of a polyol, and a methyl or ethyl ether thereof.

9. The kit according to claim 8, wherein the first composition comprises at least one of 1,2-propanediol and glycerol.

10. The kit according to claim 8, wherein the first composition comprises at least one of 1-methoxypropanol(-2) and dipropyleneglycol monomethylether.

11. A method for the permanent waving of human hair using a ready-to-use composition, comprising the steps of
    (a) mixing a first composition and a second composition to obtain the ready-to-use composition for application onto human hair,
        (1) the first composition comprising thioglycolic acid or a salt thereof, at least one amino acid hydrochloride, and at least one compound chosen from the group consisting of polyol, and a methyl or ethyl ether thereof in an aqueous solution, said first composition having a pH-value of about 4.5 to 6.5, and
        (2) the second composition comprising at least one compound chosen from the group consisting of ammonium carbonate, ammonium hydrogen carbonate and ammonium carbamate, said second composition having a pH-value of about between 8 and 9.5, whereby the ready-to-use composition has a pH-value between 7 and 8,
    (b) immediately applying the ready-to-use composition to human hair, and then
    (c) applying a neutralization compound to the hair.

12. The method according to claim 11, wherein the first composition has a pH-value between 5.0 and 6.0.

13. The method according to claim 11, wherein the second composition has a pH-value between 8.5 and 9.2.

14. The method according to claim 11, wherein the ready-to-use composition has a pH-value between 7.3 and 7.7.

15. The method according to claim 11, wherein the amino acid hydrochloride is cysteine hydrochloride.

16. The method according to claim 11, wherein the amino acid hydrochloride is glycine hydrochloride.

17. The method according to claim 11, wherein the first composition comprises 1 to 15% by weight of the at least one compound chosen from the group consisting of a polyol, and a methyl or ethyl ether thereof.

18. The method according to claim 17, wherein the first composition comprises at least one of 1,2-propanediol and glycerol.

19. The method according to claim 17, wherein the first composition comprises at least one of 1-methoxypropanol (-2) and dipropyleneglycol monomethylether.

20. The method according to claim 11, wherein the second composition comprises 1 to 5% by weight ammonium hydrogen carbonate, as a percentage of the total weight of the first and second compositions.

* * * * *